United States Patent
Lang

(10) Patent No.: US 9,517,134 B2
(45) Date of Patent: *Dec. 13, 2016

(54) IMPLANT DEVICE AND METHOD FOR MANUFACTURE

(71) Applicant: ConforMIS, Inc., Bedford, MA (US)

(72) Inventor: Philipp Lang, Lexington, MA (US)

(73) Assignee: ConforMIS, Inc., Bedford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/285,151

(22) Filed: May 22, 2014

(65) Prior Publication Data

US 2014/0250677 A1    Sep. 11, 2014

Related U.S. Application Data

(63) Continuation of application No. 13/157,857, filed on Jun. 10, 2011, now Pat. No. 8,735,773, which is a
(Continued)

(51) Int. Cl.
*A61F 2/28* (2006.01)
*A61F 2/30* (2006.01)
(Continued)

(52) U.S. Cl.
CPC .............. *A61F 2/28* (2013.01); *A61F 2/30756* (2013.01); *A61F 2/30942* (2013.01); *A61F 2/38* (2013.01);
(Continued)

(58) Field of Classification Search
CPC .......... A61F 2/30756; A61F 2/38; A61F 2/28; A61F 2/30942; A61F 2/4225; A61F 2/4202; A61F 2/32; A61F 2/3859; A61F 2/4261; A61F 2/40; A61F 2/3804; A61F 2/4241; A61F 2/44; A61F 2/389; A61F 2002/30968; A61F 2002/30957; A61F 2002/30092; A61F 2002/30884; A61F 2002/3096; A61F 2002/30892; A61F 2002/30952; A61F 2310/00023; A61F 2310/00131; A61F 2310/00029; A61F 2310/00017; A61F 2310/00239; A61F 2002/00203; A61F 2310/00161; A61F 2310/00011; A61F 2310/00179; A61F 2310/00167; A61F 2210/0014; Y10T 29/49
(Continued)

(56) References Cited

U.S. PATENT DOCUMENTS 4,673,409 A    6/1987    Van Kampen ................. 623/23
5,246,530 A    9/1993    Bugle et al. .................. 156/643
(Continued)

FOREIGN PATENT DOCUMENTS

DE    3933459 A1    4/1991    ............... A61F 2/00
DE    10055465 A1    5/2002    ............ A61L 24/00
(Continued)

OTHER PUBLICATIONS

United States Patent and Trademark Office, Office Action dated Oct. 27, 2014, pertaining to U.S. Appl. No. 13/887,712, 10 pages.
(Continued)

*Primary Examiner* — Pedro Philogene
(74) *Attorney, Agent, or Firm* — Sunstein Kann Murphy & Timbers LLP

(57) ABSTRACT

Disclosed are systems, devices and methods for optimizing the manufacture and/or production of patient-specific orthopedic implants. The methods include obtaining image data of a patient, selecting a blank implant to be optimized for the patient, and modifying the blank implant utilizing techniques disclosed herein to alter specific features of the implant to conform to the patient's anatomy.

7 Claims, 4 Drawing Sheets

Related U.S. Application Data continuation-in-part of application No. 12/031,239, filed on Feb. 14, 2008, now Pat. No. 8,617,242.

(60) Provisional application No. 61/353,386, filed on Jun. 10, 2010, provisional application No. 60/889,859, filed on Feb. 14, 2007.

(51) Int. Cl.
| | | |
|---|---|---|
| A61F 2/38 | (2006.01) | |
| A61F 2/32 | (2006.01) | |
| A61F 2/40 | (2006.01) | |
| A61F 2/42 | (2006.01) | |
| A61F 2/44 | (2006.01) | |

(52) U.S. Cl.
CPC .............. *A61F 2/32* (2013.01); *A61F 2/3804* (2013.01); *A61F 2/389* (2013.01); *A61F 2/3859* (2013.01); *A61F 2/40* (2013.01); *A61F 2/4202* (2013.01); *A61F 2/4225* (2013.01); *A61F 2/4241* (2013.01); *A61F 2/4261* (2013.01); *A61F 2/44* (2013.01); *A61F 2002/30092* (2013.01); *A61F 2002/3097* (2013.01); *A61F 2002/30884* (2013.01); *A61F 2002/30892* (2013.01); *A61F 2002/30952* (2013.01); *A61F 2002/30957* (2013.01); *A61F 2002/30968* (2013.01); *A61F 2210/0014* (2013.01); *A61F 2310/00011* (2013.01); *A61F 2310/00017* (2013.01); *A61F 2310/00023* (2013.01); *A61F 2310/00029* (2013.01); *A61F 2310/00131* (2013.01); *A61F 2310/00161* (2013.01); *A61F 2310/00167* (2013.01); *A61F 2310/00179* (2013.01); *A61F 2310/00203* (2013.01); *A61F 2310/00239* (2013.01); *Y10T 29/49* (2015.01)

(58) Field of Classification Search
USPC . 606/86 R–89, 102, 105; 29/592; 623/18.11, 20.14, 14.12, 22.11, 19.11, 623/20.35, 23.32; 600/587, 407, 424, 427, 428
See application file for complete search history.

(56) References Cited

U.S. PATENT DOCUMENTS

| | | | |
|---|---|---|---|
| 5,365,996 A | 11/1994 | Crook | 164/45 |
| 5,507,820 A | 4/1996 | Pappas | 623/20 |
| 6,251,143 B1 | 6/2001 | Schwartz et al. | 623/23.72 |
| 6,254,639 B1 | 7/2001 | Peckitt | 623/11.11 |
| 6,280,478 B1 | 8/2001 | Richter et al. | 623/23.56 |
| 6,540,786 B2 | 4/2003 | Chibrac et al. | 623/18.11 |
| 6,632,246 B1 | 10/2003 | Simon et al. | 623/14.12 |
| 6,679,917 B2 | 1/2004 | Ek | 623/20.14 |
| 6,712,856 B1 | 3/2004 | Carignan et al. | 623/20.35 |
| 6,905,514 B2 | 6/2005 | Carignan et al. | 623/20.35 |
| 6,932,842 B1 | 8/2005 | Litschko et al. | 623/16.11 |
| 6,978,188 B1 | 12/2005 | Christensen | 700/118 |
| 7,001,672 B2 | 2/2006 | Justin et al. | 428/615 |
| 7,172,596 B2 | 2/2007 | Coon et al. | 606/87 |
| 7,445,640 B2 | 11/2008 | Despres, III et al. | 623/23.53 |
| 7,603,192 B2 | 10/2009 | Martin et al. | 700/98 |
| 7,632,575 B2 | 12/2009 | Justin et al. | 428/615 |
| 7,718,109 B2 | 5/2010 | Robb et al. | 264/308 |
| 8,086,336 B2 | 12/2011 | Christensen | 700/98 |
| 8,337,508 B2* | 12/2012 | Lavallee et al. | 606/105 |
| 8,617,242 B2 | 12/2013 | Philipp | 623/16.11 |
| 8,735,773 B2* | 5/2014 | Lang | A61F 2/30756 219/121.72 |
| 2002/0059049 A1 | 5/2002 | Bradbury et al. | 703/11 |
| 2002/0079601 A1 | 6/2002 | Russell et al. | 264/40.1 |
| 2002/0082741 A1 | 6/2002 | Mazumder et al. | 700/123 |
| 2003/0080957 A1 | 5/2003 | Stewart et al. | 345/420 |
| 2003/0236473 A1 | 12/2003 | Dore et al. | 600/587 |
| 2004/0117015 A1* | 6/2004 | Biscup | 623/16.11 |
| 2005/0148843 A1 | 7/2005 | Roose | 600/407 |
| 2005/0244239 A1 | 11/2005 | Shimp | 409/132 |
| 2005/0267584 A1 | 12/2005 | Burdulis, Jr. et al. | 623/20.19 |
| 2006/0069318 A1 | 3/2006 | Keaveny et al. | 600/300 |
| 2006/0136058 A1 | 6/2006 | Pietrzak | 623/13.14 |
| 2007/0005143 A1 | 1/2007 | Ek et al. | 623/20.32 |
| 2007/0118243 A1 | 5/2007 | Schroeder et al. | 700/118 |
| 2007/0142914 A1 | 6/2007 | Jones et al. | 623/14.13 |
| 2007/0198022 A1 | 8/2007 | Lang et al. | 606/88 |
| 2007/0226986 A1* | 10/2007 | Park et al. | 29/592 |
| 2008/0004709 A1 | 1/2008 | O'Neill et al. | 623/20.35 |
| 2008/0195216 A1 | 8/2008 | Philipp | 623/18.11 |
| 2009/0131941 A1* | 5/2009 | Park et al. | 606/87 |
| 2011/0029093 A1 | 2/2011 | Bojarski et al. | 623/20.35 |
| 2011/0087332 A1 | 4/2011 | Bojarski et al. | 623/20.32 |
| 2011/0092804 A1 | 4/2011 | Schoenefeld et al. | 600/416 |
| 2011/0266265 A1 | 11/2011 | Lang | 219/121.72 |
| 2013/0245803 A1 | 9/2013 | Lang | 700/98 |
| 2014/0109384 A1 | 4/2014 | Lang | 29/557 |

FOREIGN PATENT DOCUMENTS

| | | | | |
|---|---|---|---|---|
| DE | 102006037067 A1 | 2/2008 | | C04B 41/87 |
| EP | 1683593 A2 | 7/2008 | | B22F 3/105 |
| EP | 2173260 B1 | 4/2010 | | A61B 17/15 |
| JP | 8-25487 A | 1/1996 | | B29C 67/00 |
| JP | 9-169056 A | 6/1997 | | B29C 67/00 |
| JP | 2004-166802 A | 6/2004 | | A61F 2/38 |
| JP | 2007-236926 A | 9/2007 | | A61F 2/36 |
| JP | 2010-538882 A | 12/2010 | | B29C 67/00 |
| WO | WO 2004/047688 A1 | 6/2004 | | A61F 2/30 |
| WO | WO 2005/002473 A1 | 1/2005 | | A61F 2/38 |
| WO | WO 2008/021494 A2 | 2/2008 | | G06F 19/00 |
| WO | WO 2008/101090 A2 | 8/2008 | | A61F 2/38 |
| WO | WO 2009/039159 A2 | 3/2009 | | |
| WO | WO 2009/068892 A1 | 6/2009 | | A61C 9/00 |

OTHER PUBLICATIONS

Sunstein Kann Murphy & Timbers LLP, Amendment to Office Action dated Oct. 27, 2014, pertaining to U.S. Appl. No. 13/887,712, 9 pages.
United States Patent and Trademark Office, Office Action dated May 28, 2015, pertaining to U.S. Appl. No. 13/887,712, 10 pages.
Sunstein Kann Murphy & Timbers LLP, Request for Continued Examination and Response filed Nov. 30, 2015, pertaining to U.S. Appl. No. 13/887,712, 10 pages.
United States Patent and Trademark Office, Office Action dated Mar. 7, 2016, pertaining to U.S. Appl. No. 13/887,712, 11 pages.
United States Patent and Trademark Office, Office Action dated Apr. 20, 2015, pertaining to U.S. Appl. No. 14/134,064, 9 pages.
Sunstein Kann Murphy & Timbers LLP, Amendment to Office Action dated Apr. 20, 2015, pertaining to U.S. Appl. No. 14/134,064, 12 pages.
United States Patent and Trademark Office, Office Action dated Nov. 27, 2015, pertaining to U.S. Appl. No. 14/134,064, 10 pages.
European Patent Office, Extended European Search Report—Application No. 13775348.9-1654 dated Mar. 10, 2015, 6 pages.
European Patent Office, Extended European Search Report—Application No. 12192903.8-1654 dated Apr. 17, 2013, 8 pages.
International Searching Authority, International Search Report—International Application No. PCT/US2008/053977, dated Sep. 30, 2008, together with the Written Opinion of the International Searching Authority, 17 pages.
International Searching Authority, International Search Report—International Application No. PCT/US2012/025274 dated Oct. 25, 2012, together with the Written Opinion of the International Searching Authority, 12 pages.
International Searching Authority, International Search Report—International Application No. PCT/US2013/036505 dated Jul. 29, 2013, together with the Written Opinion of the International Searching Authority, 7 pages.

(56) References Cited

OTHER PUBLICATIONS

International Searching Authority, International Search Report—International Application No. PCT/US2013/061042 dated Jan. 10, 2014, together with the Written Opinion of the International Searching Authority, 12 pages.
Sunstein Kann Murphy & Timbers LLP, Amendment to Office Action dated Feb. 25, 2015, 2015, pertaining to U.S. Appl. No. 14/051,003, 8 pages.
United States Patent and Trademark Office, Notice of Allowance dated Mar. 14, 2016, pertaining to U.S. Appl. No. 14/051,003, 5 pages.
International Searching Authority, International Search Report—International Application No. PCT/US2013/035536 dated Jul. 18, 2013, together with the Written Opinion of the International Searching Authority, 9 pages.
European Patent Office, Partial Supplementary European Search Report—Application No. 13771863.1-1654, dated Apr. 26, 2016, 7 pages.
U.S. Appl. No. 13/746,742, filed Jan. 22, 2013.
U.S. Appl. No. 13/887,712, filed May 6, 2013.
U.S. Appl. No. 14/033,095, filed Sep. 20, 2013.
U.S. Appl. No. 14/033,350, filed Sep. 20, 2013.
U.S. Appl. No. 14/051,003, filed Oct. 10, 2013.
U.S. Appl. No. 14/134,064, filed Dec. 19, 2013.
U.S. Appl. No. 14/216,473, filed Mar. 17, 2014.
U.S. Appl. No. 14/390,829, filed Apr. 13, 2013.

\* cited by examiner

IMPLANT DEVICE AND METHOD FOR
MANUFACTURE

CROSS-REFERENCE TO RELATED APPLICATIONS

This application is a continuation of U.S. application Ser. No. 13/157,857, filed on Jun. 10, 2011, entitled "Implant Device and Method for Manufacture," which in turn claims the benefit of priority to U.S. Provisional Patent Application No. 61/353,386, filed on Jun. 10, 2010, entitled "Production of Patient-Specific Implants," the disclosures of which are both herein incorporated by reference in their entireties.

U.S. application Ser. No. 13/157,857 is also a continuation-in-part of U.S. patent application Ser. No. 12/031,239 filed Feb. 14, 2008, entitled, "Implant Device and Method for Manufacture," which in turn claims priority to U.S. Provisional Patent Application No. 60/889,859, filed on Feb. 14, 2007, entitled "Implant Device and Method for Manufacture," the disclosures of which are herein incorporated by reference in their entireties.

All of the above patent applications, as well as patent applications and other references mentioned hereinbelow, are hereby incorporated by reference in their entireties.

FIELD OF THE INVENTION

Disclosed are methods, systems and devices of making improved and/or patient-adapted (e.g., patient-specific and/or patient-engineered) orthopedic implants and methods for manufacture in a cost effective and timely manner. Applicants' disclosure utilizes and incorporates various technologies and advances, including medical imaging, computer-aided design and additive and/or subtractive manufacturing processes, production forecasting and financial and cost modeling to produce an orthopedic implant.

BACKGROUND OF THE INVENTION

Joint implants are well known in the art. For example, one of the most common types of joint prosthetic devices is a knee implant including a femoral component and a tibial component. Other common joint implants are associated with, for example, the hip and shoulder, although many other implant locations are contemplate by the present disclosure, including the spine, spinal articulations, intervertebral discs, facet joints, shoulder joints, elbows, wrists, hands, finger joints, ankles, wrists, feet and toe joints.

The shape and size of various joint implants are becoming increasingly more complex and may include, for example, one or more concavities and/or convexities, as described in various literature, including U.S. patent application Ser. No. 10/997,407, filed on Nov. 24, 2004, the disclosure of which is incorporated by reference herein. Traditional implant manufacturing processes, which may even include manual steps, and which may be satisfactory for less complex shaping, are becoming inadequate. Traditionally, a diseased, injured or defective joint, such as, for example, a joint exhibiting osteoarthritis, would be repaired using standard off-the-shelf implants and other surgical devices. The drawback to this approach is that typically a decision must be made between devices that are either too large or too small or otherwise just not the right shape for the patient's anatomy. In order to make one of these sub-optimal devices fit properly, a surgeon must typically remove an undesirable or unacceptable amount of healthy or undamaged tissue from the surgical site, or accept using an implant that is not optimally sized or capable of being well positioned for the patient—settling for an implant and surgery that is "good enough" in the surgeon's estimation.

Furthermore, joint implants, such as a knee implant that includes tibial and femoral components, often require a relatively large cut on, for example, the tibia. This is due, in part, to satisfy a desired minimum thickness (for strength and/or reliability) of the materials of the component, such as polyurethane for a portion of a tibial component. The cut on the tibia, upon which the tibial component rests, provides space for the desired thickness of the polyurethane tibial component, desirably without overstuffing the joint. Such cuts can often be highly invasive, resulting in loss of valuable bone stock, and over time, osteolysis frequently leads to loosening of the prosthesis. Further, the area where the implant and the bone mate will typically degrade over sufficient time and loading cycles, requiring that the prosthesis be replaced. Since the patient's bone stock is limited, the number of possible replacement surgeries is also limited to a generally finite number of joint arthroplasties.

There are now various custom-made, patient-specific orthopedic implants known in the art, and such implants can be developed using software modeling programs. Such patient-specific implants, such as the iForma®, iUni® and iDuo® (commercially available from ConforMIS, Inc., Burlington, Mass.), offer advantages over the traditional "several-sizes-fit-all" approach such as a better fit, more natural movement, reduction in the amount of bone removed during surgery and a less invasive procedure. Such patient-specific implants generally can be created from images of the patient's joint and/or surrounding anatomical structures. Based on the images, the patient-specific implant can be created both to include surfaces that match existing surfaces in the joint, as well as to include surfaces that approximate an ideal and/or healthy surface that may not exist in the patient prior to any procedure. However, this patient-specific, tailor-made approach can be costly, both in terms of money and time. There remains a need in the art, therefore, for systems and methods of designing, manufacturing and implanting implants, including custom-made or modular implants as well as custom, patient-specific implants, in a more timely and cost effective manner.

SUMMARY OF THE INVENTION

The disclosures herein provide systems and methods for designing, manufacturing and implanting orthopedic implants. Various methods include obtaining a three-dimensional image of a patient's joint, selecting a standard blank implant and modifying the blank to incorporate features that are specific and/or desirable to that patient. Various embodiments provide methods for making implants suitable for a joint, including providing a blank with a (i.e., at least one) dimension smaller than the desired implant size and/or shape, and material is added to the blank so as to form surface or other details on the implant. In related embodiments, adding material to the blank may include laser sintering and/or electron beam melting. Adding material to the blank may include adding ceramic(s), metal(s) and/or ceramic-metal composite(s). The material added to the blank may be polished. In further embodiments, the blank may be made of, e.g., polymer(s), metal(s), cross-linked polymer(s), ceramic(s), ceramic-metal composite(s), and/or alloy(s); or use-appropriate combinations thereof. Providing the blank may include forming the blank by casting and/or milling. In still further embodiments, a three-dimensional shape (i.e., at least one, or a portion of at least one) of a surface of the joint is determined. Determining the three-dimensional shape may include the use of imaging, such as MRI, CT, ultrasound, digital tomosynthesis, and/or optical coherence techniques. The material added to the blank may be, in various embodiments, such that a surface of the implant is formed as a substantial negative of and/or in a mirror image of a corresponding surface of the joint. Alternatively, the surface of the implant may conform to the corresponding surface of the joint, and may conform exactly or the conforming shape may be "filtered" or otherwise altered, yet still permit the implant to maintain substantial contact with an unmodified or modified joint surface. The implant may be, e.g., a cartilage repair, unicompartmental knee, bicompartmental knee, total knee replacement, hip, shoulder, or interpositional joint implant. An interpositional joint implant may be associated with, e.g., a knee, hip or shoulder or other joint as disclosed and contemplated herein.

Other embodiments describe a method for making an implant suitable for a joint including providing a blank having a dimension that is different from the implant. The blank is modified by removing material, such as by using, at least in part, a laser, and/or electron beam melting to form the implant. The formed surfaces may desirably be polished. In related embodiments, the blank may include a dimension that is larger than the implant, and wherein modifying the blank includes cutting the blank with the laser. Laser-cut surfaces may desirably be polished. In further related embodiments, the blank may include a dimension that is smaller than the implant, and wherein modifying the blank includes adding material by laser sintering. The added material may be desirably polished. The blank may be made of polymer(s), metal(s), cross-linked polymer(s), ceramic(s), ceramic-metal composite(s), and/or alloy(s); or use-appropriate combinations thereof. The blank may be formed by casting and/or milling. In related embodiments, a three-dimensional shape of a (i.e., at least one, or a portion of at least one) surface of the joint may be determined. Determining the three-dimensional shape may include the use of imaging, such as MRI, CT, ultrasound, digital tomosynthesis, and/or optical coherence techniques. The blank may be desirably modified such that a surface of the implant is substantially a negative of and/or a mirror image of a corresponding surface of the joint.

The disclosed methods may include the selection of implants having combinations of larger and/or smaller or other dimensions than a desired implant, including one or more portion(s) that are smaller than a desired dimension, and other portion(s) that are larger than desired. In such a case, various additive and subtractive steps, as herein disclosed, may be utilized to render the implant more suitable for the targeted anatomy.

In accordance with other embodiments, methods for making an implant suitable for a joint include providing blanks with at least one dimension larger than the desired or target implant. A laser, polishing, etching, milling and/or an abrading process is used to cut the blank so as to form surface detail of the implant. In related embodiments, the blank may be made of polymer(s), metal(s), cross-linked polymer(s), ceramic(s), ceramic-metal composite(s), and/or alloy(s); or use-appropriate combinations thereof. Providing the blank may include forming the blank by casting and/or milling.

In still further embodiments, a three-dimensional shape (i.e., at least one, or a portion of at least one) of a surface of the joint is determined. Determining the three-dimensional shape may include the use of imaging, such as MRI, CT, ultrasound, digital tomosynthesis, and/or optical coherence, and may further include computer modeling of the joint, opposing joints, and/or data from normalized or healthy joints. The blank may be desirably cut such that a surface of the implant is substantially a negative of or conforms to a corresponding surface of the joint. The implant may be, e.g., a cartilage repair, unicompartmental knee, bicompartmental knee, total knee replacement, hip, shoulder, or interpositional joint implant. An interpositional joint implant may be associated with, e.g., a knee, hip or shoulder, or other joints as previously discussed.

The field of the rapid prototyping of parts has, in recent years, made large improvements in broadening high strain, high density parts for use in the design and pilot production of many useful articles, including metal parts. The technologies have also been applied to the direct fabrication of articles, such as molds, from metal powders without a binder. Preferred metals for the powder include titanium, titanium alloys, stainless steel, cobalt chrome alloys, tantalum or niobium. The metal articles formed in these ways have been quite dense, for example, having densities of up to 70% to 80% of fully dense (prior to any infiltration). Prior applications of this technology have strived to increase the density of the metal structures formed by the remelting or sintering processes. The field of rapid prototyping of parts has focused on providing high strength, high density, parts for use and design in production of many useful articles, including metal parts.

In one embodiment, the method comprises (a) obtaining image data of a patient's joint; (b) providing a blank with a (i.e. at least one) dimension smaller than the implant; and (c) adding material to the blank so as to form surface detail on the implant. Adding material to the blank may include adding ceramic(s), metal(s) and/or ceramic-metal composite(s). The material added to the blank may be polished, also. In further embodiments, the blank may be made of, e.g. polymer(s), metal(s), cross-linked polymer(s), ceramic(s), ceramic-metal composite(s), and/or alloy(s); or use-appropriate combinations thereof.

Various embodiments relate to methods for forming or creating patient-adapted implants. Patient-adapted features of an implant component can be achieved by analyzing imaging test data and selecting, designing or modifying (e.g., preoperatively selecting from a library, preoperatively modifying or preoperatively designing) an implant component having at least one feature that is matched and/or optimized for the particular patient's biology. Accordingly, the patient-adapted implant components include one or more patient-adapted features.

In still further embodiments, a three-dimensional shape (i.e. at least one, or a portion of at least one) of a surface of the joint is determined. Determining the three-dimensional shape may include the use of imaging, such as MRI, CT, ultrasound, digital tomosynthesis, and/or optical coherence techniques, and may further include computer modeling of the joint, opposing joints, and/or data from normalized or healthy joints. The material added to the blank may be, in embodiments, such that a surface of the implant conforms to a corresponding surface of the joint. The implant may be, e.g. a cartilage repair, unicompartmental knee, bicompartmental knee, total knee replacement, hip, shoulder, or interpositional joint implant.

Other embodiments provide methods for making implants suitable for a joint including providing a blank having a dimension that is different from the implant. The blank is modified in some manner, including using, in various embodiments, at least in part, a laser, and/or electron beam melting to form the implant. The formed surfaces may desirably be polished. In related embodiments, the blank may include a dimension that is larger than the implant, and wherein modifying the blank includes cutting the blank with the laser. Laser-cut surfaces may desirably be polished. In further related embodiments, the blank may include a dimension that is smaller than the implant, and wherein modifying the blank includes adding material by laser sintering. The added material may be desirably polished. The blank may be made of polymer(s), metal(s), cross-linked polymer(s), ceramic(s), ceramic-metal composite(s), and/or alloy(s); or use-appropriate combinations thereof. The blank may be formed by casting and/or milling. In related embodiments, a three-dimensional shape of a (i.e., at least one, or a portion of at least one) surface of the joint may be determined. Determining the three-dimensional shape may include the use of imaging, such as MRI, CT, ultrasound, digital tomosynthesis, and/or optical coherence techniques. The blank may be desirably modified such that a surface of the implant conforms to a corresponding surface of the joint.

In accordance with another embodiment, a method for making an implant suitable for a joint includes providing a blank with at least one dimension larger than the implant. A laser, polishing, etching, milling and/or an abrading process is used to cut the blank so as to form surface detail of the implant. In related embodiments, the blank may be made of polymer(s), metal(s), cross-linked polymer(s), ceramic(s), ceramic-metal composite(s), and/or alloy(s); or use-appropriate combinations thereof. Providing the blank may include forming the blank by casting and/or milling.

In still further embodiments, a three-dimensional shape (i.e., at least one, or a portion of at least one) of a surface of the joint is determined. Determining the three-dimensional shape may include the use of imaging, such as MRI, CT, ultrasound, digital tomosynthesis, and/or optical coherence, and may further include computer modeling of the joint, opposing joints, and/or data from normalized or healthy joints. The blank may be desirably cut such that a surface of the implant conforms to a corresponding surface of the joint. The implant may be, e.g., a cartilage repair, unicompartmental knee, bicompartmental knee, total knee replacement, hip, shoulder, or interpositional joint implant. An interpositional joint implant may be associated with, e.g., a knee, hip or shoulder.

In accordance with another embodiment, a knee implant includes a femoral component having first and second femoral component surfaces. The first femoral component surface is for securing to a surgically prepared compartment of a distal end of a femur. The second femoral component surface is configured to replicate the femoral condyle. The knee implant further includes a tibial component having first and second tibial component surfaces. The first tibial component surface is for contacting a proximal surface of the tibia that is substantially uncut subchondral bone (which may further include overlying articular cartilage.) At least a portion of the first tibial component surface conforms to a corresponding proximal tibial surface. The second tibial component surface articulates with the second femoral component surface. In related embodiments, the second femoral component surface may include at least one of a ceramic and a metal, and the second tibial component surface may include ceramic(s) and/or metal(s). Both the second femoral component surface and the second tibial surface may include metal(s). Both the second femoral component surface and the second tibial surface may include ceramic(s).

The second femoral component surface may include one of a ceramic and a metal, and the second tibial surface may include the other of the one of a ceramic and a metal, e.g., the second femoral component surface may be ceramic, and the second tibial surface may be metal. The tibial component may have a thickness of 3 mm or less.

In accordance with another embodiment, a knee implant includes a femoral component having first and second femoral component surfaces. The first femoral component surface is for securing to a surgically prepared compartment of a distal end of a femur. The second femoral component surface is configured to replicate the femoral condyle. The knee implant further includes a tibial component having first and second tibial component surfaces. The first tibial component surface is for contacting a proximal surface of the tibia that is substantially uncut subchondral bone (which may further include overlying articular cartilage). In alternative embodiments, the surface may be cut bone. At least a portion of the first tibial component surface is substantially a negative of a corresponding proximal tibial surface. The second tibial component surface articulates with the second femoral component surface. In related embodiments, the second femoral component surface may include at least one of a ceramic and a metal, and the second tibial component surface may include ceramic(s) and/or metal(s). Both the second femoral component surface and the second tibial surface may include metal(s). Both the second femoral component surface and the second tibial surface may include ceramic(s).

The second femoral component surface may include one of a ceramic and a metal, and the second tibial surface may include the other of the one of a ceramic and a metal, e.g., the second femoral component surface may be ceramic, and the second tibial surface may be metal. The tibial component may have a thickness of 3 mm or less.

In related embodiments, the tibial component may include an anchoring mechanism, such as a peg and/or a keel. Alternatively, the tibial component may be an interpositional implant that does not include a physical anchoring mechanism.

In additional embodiments, a desired three-dimensional shape (i.e., at least one, or a portion of at least one) of a surface of the joint is determined. Determining the three-dimensional shape may include the use of imaging, such as MRI, CT, ultrasound, digital tomosynthesis, and/or optical coherence, and may further include computer modeling of the joint, opposing joints, and/or data from normalized or healthy joints. From the 3-D joint model, one or more "suitable" implant shapes and/or sizes (i.e., one or more implants that can be altered using the various methods disclosed herein to approximate a size/shape appropriate to the determined three-dimensional shape) may be determined and/or identified. The determined/identified implant(s) are then compared and evaluated against the desired shape, and the required modifications for each respective implant is identified and evaluated. Each "suitable" implant is then evaluated to determine a variety of factors, including cost of modification, equipment/facilities necessary to modify said implant, time and expertise necessary to modify said implant, geographical constraints (i.e., implant, equipment, patient and surgical center location, among other factors), current workload, blank inventory and availability, or other factors relevant to the manufacturing and modification expenses. The factors may then be compared and/or rated, and a "suitable" implant chosen for actual manufacture and modification. The implant "blanks" may be pre-manufactured, although concurrent blank manufacturing is contemplated herein. The blank may be desirably cut or have material added such that a surface of the implant conforms to a corresponding surface of the joint. The implant may be, e.g., a cartilage repair, unicompartmental knee, bicompartmental knee, total knee replacement, hip, shoulder, or interpositional joint implant. An interpositional joint implant may be associated with, e.g., a knee, hip or shoulder.

The methods of designing, making, and using the implants described herein can be applied to any joint including, without limitation, a spine, spinal articulations, an intervertebral disk, a facet joint, a shoulder joint, an elbow, a wrist, a hand, a finger joint, a hip, a knee, an ankle, a foot, or a toe joint.

BRIEF DESCRIPTION OF THE DRAWINGS

The foregoing features of the inventions will be more readily understood by reference to the following detailed description, taken with reference to the accompanying drawings, in which.

DETAILED DESCRIPTION OF THE INVENTION AND EMBODIMENTS

Disclosed are systems and methods for making joint implants that leverage additive or subtractive manufacturing methods including laser sintering and electron beam melting, and to less-invasive and/or non-invasive joint implants which may be advantageously made by the methods described herein. Such implants may feature a surface of the implant that is advantageously a mirror image of, substantially a negative of or formed in a shape that substantially conforms to the joint surface, or combinations thereof. In other embodiments, non-invasive or less-invasive joint implants that rest on substantially uncut subchondral bone are described. Detailed disclosures are now described in further detail, below.

As used herein and in the appended claims, the singular forms "a", "an", and "the" include plural references unless the context clearly dictates otherwise. Thus, for example, reference to "a device" includes a plurality of such devices and equivalents thereof known to those skilled in the art, and so forth. Similarly, the terms "a" (or "an"), "one or more" and "at least one" can be used interchangeably herein. Also, the terms "comprising", "including", and "having" can be used interchangeably.

It is to be understood that the implants described herein may be associated with a wide variety of joints, including, without limitation, joint implants used in a knee, shoulder, hip, vertebrae, elbow, ankle, hand, foot and wrist.

Figure 1:
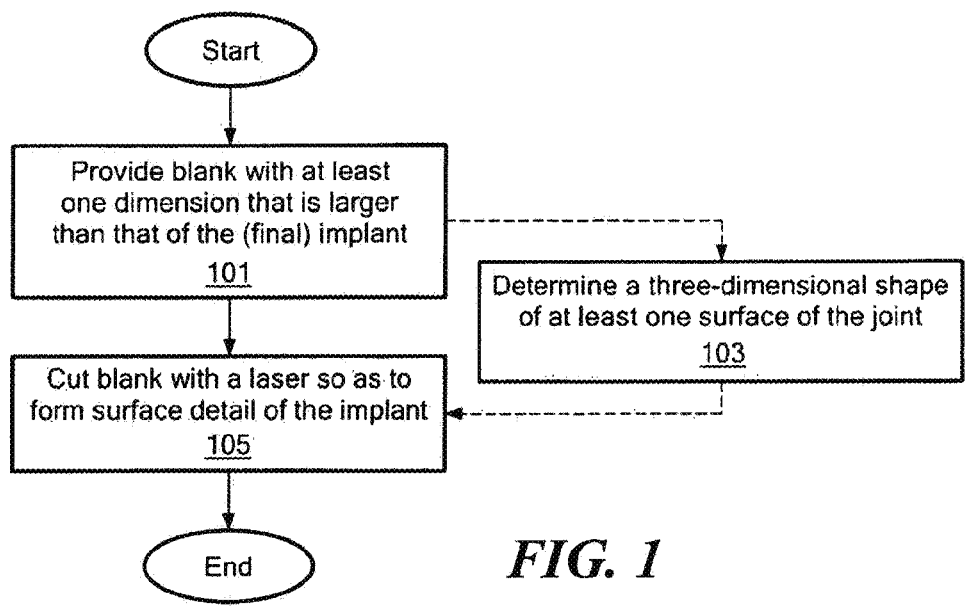
FIG. 1 is a flowchart depicting an embodiment of a method for manufacturing a joint implant.

FIG. 1 is a flowchart depicting a method for manufacturing a joint implant, in accordance with one embodiment. In this method, a desired three-dimensional shape (i.e., at least one, or a portion of at least one) of a surface of the joint can be determined 103. Determining the three-dimensional shape may include the use of imaging, such as MRI, CT, ultrasound, digital tomosynthesis, and/or optical coherence, and may further include computer modeling of the joint, opposing joints, and/or data from normalized or healthy joints. From the 3-D joint model, one or more "suitable" implant shapes and/or sizes (i.e., one or more implants that can be altered using the various methods disclosed herein to approximate a size/shape appropriate to the determined three-dimensional shape) may be determined and/or identified. Alternatively, or in addition to the joint analysis, a desired implant or "final" implant shape can be selected, or it can be derived from this shape and blank information from step 103. Desirably, a blank is provided 101 with at least one dimension that is larger than that of a desired or "final" implant. The dimension of the implant may be, e.g., a partial or uniform thickness, length, width, or curvature. The blank may be made of, without limitation, a polymer, a metal, a cross-linked polymer, a ceramic, a ceramic-metal composite, and/or an alloy.

Suitable materials for use in joint implants and methods described herein can include metals and metal alloys including CoCrMo, CoCr, titanium alloys and commercially pure TI (cpTi), medical grade stainless steels, tantalum and tantalum alloys, and Nitinol ("NiTi"). Particularly advantageous materials are those well-suited, or specifically designed, for laser sintering or electron-beam melting manufacturing techniques, e.g., ASTM F-75 CoCr alloy, or Arcam Ti6Al4V ELI titanium alloy (available from Stratasys, Eden Prairie, Minn.). Ceramic materials, e.g., aluminum oxide or alumina, zirconium oxide or zirconia, compact of particulate diamond, and/or pyrolytic carbon may be used.

An example of a modern rapid prototyping technology is the selective laser sintering process practiced by systems available from DTM Corporation of Austin, Tex. According to this technology, articles are produced in layer-wise fashion from a laser-fusible powder that is dispensed one layer at a time. The powder is fused, remelted or sintered, by the application of laser energy that is directed in raster-scan fashion to portions of the powder layer corresponding to a cross section of the article. After the fusing of the powder in each layer, an additional layer of powder is dispensed, and the process repeated, with fused portions or lateral layers fusing so as to fuse portions of previous laid layers until the article is complete. Detailed descriptions of the selective laser sintering technology may be found in U.S. Pat. Nos. 4,863,538, 5,017,753, 5,076,869 and 4,944,817, all assigned to Board of Regents, the University of Texas, each of which is hereby incorporated herein by reference in its entirety.

In various embodiments, the blank is chosen such that it is, in one or more portions, only slightly larger than that of the implant. For example, the blank may have been initially milled or cast such that all, or certain portions of the blank, are only slightly larger than the implant. Providing a blank from which material will be removed to arrive at the precise implant size, geometry and surface characteristics, potentially simplifies manufacturing processing and may ensure reproducibility. The blank may be provided, e.g., by casting, milling, forging, compression molding, extruding or injection molding.

In various embodiments, a library of blanks may be kept of varying size and shapes. Upon determining an implant size, an appropriately sized blank may then be chosen. Alternatively, an appropriate blank may be manufactured in anticipation of immediate or future need, such as in a "just in time" type of manufacturing and inventory system.

Upon providing an appropriated sized and dimensioned blank, the blank is cut with a laser or other device so as to form a shape of at least surface detail of the implant 105. Separately, or in addition to laser cutting, the blank may also be cut using precision milling or grinding, or other abrading processes known in the art. For example, after cutting the blank with the laser, the surface of the blank may desirably be polished.

As previously noted, various embodiments of the present method can include determining a three-dimensional shape of at least one surface of the joint, as shown in step 103. Using the three-dimensional shape, the blank may be cut in step 105 such that a surface of the implant, or a portion thereof, is substantially a negative image of (or alternatively may conform to) the corresponding joint surface (or portion thereof). For example, the implant surface may comprise a surface that is a substantial negative image of (or conforms to) the joint surface to which the implant surface is designed to mate, so that the implant surface mirrors or conforms to the joint surface, ensuring that the device fits the joint surface in precisely the correct location. The implant surface may alternately comprise more than one such negative or mirror image or conforming surfaces, e.g., to assist in placement in the device, i.e., the implant surface need not comprise one contiguous mirror/conforming surface to the joint surface. A series or pattern of smaller implant negative/conforming surfaces, each corresponding to or matching an area of the joint surface, can similarly be provided. Without limitation, one application of this method could include providing grooves in the implant into which cement for affixing the device may be applied or reside, so the device may be attached to the joint surface without cement flowing onto other areas of the implant surface. Another non-limiting application would be where a continuous conforming surface were not necessary, e.g., where the device may be properly seated by matching two, three, four or more conforming "reference surfaces" to corresponding areas of the joint surface. The area of the substantially negative (or conforming) surface desirably should be sufficient to ensure that the device is located properly. Where there are more than one of these "reference surfaces", the area of each should be use and application-appropriate, but a range of 1, 2, 3, 4, 5 cm² or more for each reference surface is contemplated. Where there is one implant surface with a substantially negative surface (or conforming surface), smaller areas comprising a substantial negative or conforming surface are possible, as well as the entire implant surface. Combinations of uncut and cut surfaces, and their corresponding conforming or substantial negative or mirror image implant surfaces, may be utilized as well. The joint surface may include at least one concavity and/or convexity.

Using the approach generally outlined in FIG. 1, a non-invasive joint implant, such as those described in above-mentioned U.S. application Ser. No. 10/997,407, may be manufactured. The implant may be, for example, a cartilage repair implant, a unicompartmental knee implant, a bicompartmental knee implant, a total knee replacement implant, a hip implant, and a shoulder implant. The implant may also be an interpositional implant, such as the implant described in U.S. Application No. 60/784,255.

As previously noted, determining the three-dimensional shape of the joint surface may include a wide variety of imaging methodologies. For example, the imaging may include MRI, CT, ultrasound, digital tomosynthesis, and/or optical coherence. Reference is made to U.S. application Ser. Nos. 10/997,407 and 10/728,731 for how imaging technologies are used to derive the three-dimensional shape of the joint surface. The 3-D information is then used in the CAD/CAM system to form the implant shape, geometry, and surfaces to make the desired implant.

Figure 2:
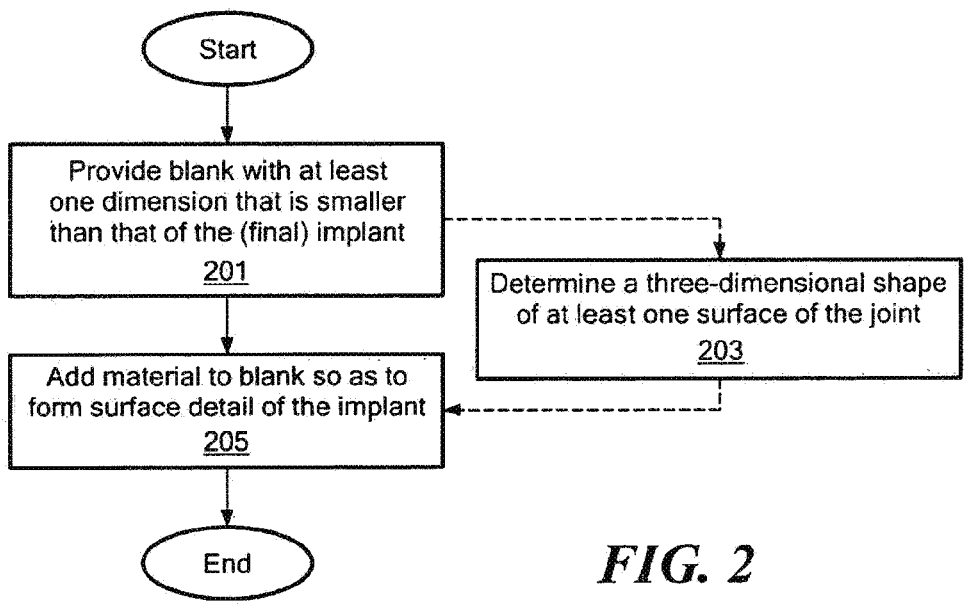
FIG. 2 is a flowchart depicting an embodiment of a method for manufacturing a joint implant.

FIG. 2 is a flowchart depicting a method for manufacturing a joint implant, in accordance with another embodiment. In step 201, a blank is provided with at least one dimension that is smaller than that of the (final) implant. The dimension of the implant may be, e.g. a partial or uniform thickness, length, width, or curvature. The blank may be made of, without limitation, a polymer, a metal, a crosslinked polymer, a ceramic, a ceramic-metal composite, and/or an alloy. A three-dimensional shape of at least one surface of a patient's joint is desirably obtained in step 203. Using laser sintering, material can be added to the blank, which has at least one dimension smaller than that of the final implant, making it conform to the size and shape of the patient's joint in step 205. If required, material can further be added to the block to form surface detail on the implant (step 205.)

The material may be added to the block using additive manufacturing technologies including laser sintering and/or electron beam melting. In laser sintering, a high power laser, such as a carbon dioxide laser, is used to fuse small particles of plastic, metal, or ceramic powders into a mass representing a desired three-dimensional object. Generally, the laser selectively fuses powdered material by scanning cross-sections generated from a 3-D digital description of the part (e.g., from a CAD file or scan data) on the surface of a powder bed. After each cross-section is scanned, the powder bed is lowered by one layer thickness, a new layer of material is applied on top, and the process is repeated until the part is completed. Laser sintering can produce parts from a relatively wide range of commercially available powder materials, including polymers, ceramics, and metals (such as steel, titanium, alloys and composites)

Full melting, partial melting, or liquid-phase sintering may be used. Electron beam melting involves melting or fusing metal, ceramic or other various powders, so as to build the part layer by layer. Exemplary electron beam melting systems are available from Stratasys, Eden Prairie, Minn.

After adding material to the blank, the surface of the blank may be desirably polished. Furthermore, and similar to above-described embodiments, the method may further include determining a three-dimensional shape of at least one surface of the joint, step 203. Using the three-dimensional shape, material may be added to the blank in step 205 such that at least one surface of the implant is substantially a negative of, a mirror image of and/or conforms to at least one surface of the joint. The implant may be, for example, a cartilage repair implant, a unicompartmental knee implant, a bicompartmental knee implant, a total knee replacement implant, a hip implant, and a shoulder implant. The implant may also be an interpositional implant, such as the implant described in U.S. Application No. 60/784,255.

Implant components can be generated using any technique known in the art today, as well as by newly developing techniques. Such techniques include, but are not limited to standard casting, molding and machining processes, as well as other processes listed in Table 1.

TABLE 1

Exemplary techniques for forming a patient-specific, patient-engineered and/or standard blank implant component for a patient's anatomy

| Technique | Brief description of technique and related notes |
| --- | --- |
| CNC | CNC refers to computer numerically controlled (CNC) machine tools, a computer-driven technique, e.g., computer-code instructions, in which machine tools are driven by one or more computers. Embodiments of this method can interface with CAD software to streamline the automated design and manufacturing process. |
| CAM | CAM refers to computer-aided manufacturing (CAM) and can be used to describe the use of software programming tools to efficiently manage manufacturing and production of products and prototypes. CAM can be used with CAD to generate CNC code for manufacturing three-dimensional objects. |
| Casting, including casting using rapid prototyped casting patterns | Casting is a manufacturing technique that employs a mold. Typically, a mold includes the negative of the desired shape of a product. A liquid material is poured into the mold and allowed to cure, for example, with time, cooling, and/or with the addition of a solidifying agent. The resulting solid material or casting can be worked subsequently, for example, by sanding or bonding to another casting to generate a final product. |
| Welding | Welding is a manufacturing technique in which two components are fused together at one or more locations. In certain embodiments, the component joining surfaces include metal or thermoplastic and heat is administered as part of the fusion technique. |
| Forging | Forging is a manufacturing technique in which a product or component, typically a metal, is shaped, typically by heating and applying force. |

Freeform fabrication is a set of manufacturing processes that produce solid 3D objects by building up successive 2D layers. The field of freeform fabrication has seen many important recent advances in the fabrication of articles directly from computer controlled databases. These advances, many of which are in the field of rapid prototyping of articles such as prototype parts and mold dies, exhibit advantages, such as greatly reduced time and expense required to fabricate articles and elimination of custom fixtures, over conventional machining processes in which a block of material, such as a metal, is machined according to engineering drawings. Exemplary techniques for manufacturing and/or adapting an implant to a patient's anatomy (such as creating three dimensional surface contours) include, but are not limited to those shown in Table 2.

TABLE 2

Exemplary techniques for forming or altering a patient-specific and/or patient-engineered implant component for a patient's anatomy

| Technique | Brief description of technique and related notes |
| --- | --- |
| Rapid prototyping | Rapid prototyping refers generally to automated construction of a prototype or product, typically using an additive manufacturing technology, such as EBM, SLS, SLM, SLA, DMLS, 3DP, FDM and other technologies |
| EBM | EBM refers to electron beam melting (EBM), which is a powder-based additive manufacturing technology. Typically, successive layers of metal powder are deposited and melted with an electron beam in a vacuum. |
| SLS | SLS refers to selective laser sintering (SLS), which is a powder-based additive manufacturing technology. Typically, successive layers of a powder (e.g., polymer, metal, sand, or other material) are deposited and melted with a scanning laser, for example, a carbon dioxide laser. |
| SLM | SLM refers to selective laser melting ™ (SLM), which is a technology similar to SLS; however, with SLM the powder material is fully melted to form a fully-dense product. |
| SLA or SL | SLA or SL refers to stereolithography (SLA or SL), which is a liquid-based additive manufacturing technology. Typically, successive layers of a liquid resin are exposed to a curing, for example, with UV laser light, to solidify each layer and bond it to the layer below. This technology typically requires the additional and removal of support structures when creating particular geometries. |
| DMLS | DMLS refers to direct metal laser sintering (DMLS), which is a powder-based additive manufacturing technology. Typically, metal powder is deposited and melted locally using a fiber optic laser. Complex and highly accurate geometries can be produced with this technology. This technology supports net-shaping, which means that the product generated from the technology requires little or no subsequent surface finishing. |
| LC | LC refers to LaserCusing ® (LC), which is a powder-based additive manufacturing technology. LC is similar to DMLS; however, with LC a high-energy laser is used to completely melt the powder, thereby creating a fully-dense product. |
| 3DP | 3DP refers to three-dimensional printing (3DP), which is a high-speed additive manufacturing technology that can deposit various types of materials in powder, liquid, or granular form in a printer-like fashion. Deposited layers can be cured layer by layer or, alternatively, for granular deposition, an intervening |

TABLE 2-continued

Exemplary techniques for forming or altering a patient-specific
and/or patient-engineered implant component for a patient's anatomy

| Technique | Brief description of technique and related notes |
|---|---|
| | adhesive step can be used to secure layered granules together in bed of granules and the multiple layers subsequently can be cured together, for example, with laser or light curing. |
| LENS | LENS ® refers to Laser Engineered Net Shaping ™ (LENS ®), which is powder-based additive manufacturing technology. Typically, a metal powder is supplied to the focus of the laser beam at a deposition head. The laser beam melts the powder as it is applied, in raster fashion. The process continues layer by and layer and requires no subsequent curing. This technology supports net-shaping, which means that the product generated from the technology requires little or no subsequent surface finishing. |
| FDM | FDM refers to fused deposition modeling ™ (FDM) is an extrusion-based additive manufacturing technology. Typically, beads of heated extruded polymers are deposited row by row and layer by layer. The beads harden as the extruded polymer cools. |
| LASER CLADDING | Laser cladding injects a powder, normally of a metallic nature, into the system by either coaxial or lateral nozzles. The interaction of the metallic powder stream and the laser causes melting to occur, and is known as the melt pool. This is deposited onto a substrate; moving the substrate allows the melt pool to solidify and thus produces a track of solid metal. |

Various of the above-listed technologies, as applied to manufacturing implants, are available from various sources, including, for example, as described in Wohlers Report 2009, State of the Industry Annual Worldwide Progress Report on Additive Manufacturing, Wohlers Associates, 2009 (ISBN 0-9754429-5-3), available from www.wohlersassociates.com; Pham and Dimov, Rapid manufacturing, Springer-Verlag, 2001 (ISBN 1-85233-360-X); Grenda, Printing the Future, The 3D Printing and Rapid Prototyping Source Book, Castle Island Co., 2009; Virtual Prototyping & Bio Manufacturing in Medical Applications, Bidanda and Bartolo (Eds.), Springer, Dec. 17, 2007 (ISBN: 10: 0387334297; 13: 978-0387334295); Bio-Materials and Prototyping Applications in Medicine, Bartolo and Bidanda (Eds.), Springer, Dec. 10, 2007 (ISBN: 10: 0387476822; 13: 978-0387476827); Liou, Rapid Prototyping and Engineering Applications: A Toolbox for Prototype Development, CRC, Sep. 26, 2007 (ISBN: 10: 0849334098; 13: 978-0849334092); Advanced Manufacturing Technology for Medical Applications: Reverse Engineering, Software Conversion and Rapid Prototyping, Gibson (Ed.), Wiley, January 2006 (ISBN: 10: 0470016884; 13: 978-0470016886); and Brauner et al., "Coupled Field Simulation in Additive Layer Manufacturing," 3rd International Conference PMI, 2008 (10 pages), each of which is hereby incorporated herein by reference in its entirety.

Joint repair systems often employ metal and/or polymeric materials including, for example, prostheses which are anchored into the underlying bone (e.g., a femur in the case of a knee prosthesis). See, e.g., U.S. Pat. No. 6,203,576 to Afriat et al. issued Mar. 20, 2001 and U.S. Pat. No. 6,322,588 to Ogle, et al. issued Nov. 27, 2001, each of which are hereby incorporated herein by reference in its entirety, and references cited therein. A wide variety of metals is useful in the practice of the present concept, and can be selected based on any criteria. For example, material selection can be based on resiliency to impart a desired degree of rigidity. Non-limiting examples of suitable metals include silver, gold, platinum, palladium, iridium, copper, tin, lead, antimony, bismuth, zinc, titanium, cobalt, stainless steel, nickel, iron alloys, cobalt alloys, such as Elgiloy®, a cobalt-chromium-nickel alloy, and MP35N, a nickel-cobalt-chromium molybdenum alloy, and Nitinol T™, a nickel-titanium alloy, aluminum, manganese, iron, tantalum, crystal free metals, such as LiquidMetal® alloys (available from LiquidMetal Technologies, www.liquidmetal.com), other metals that can slowly form polyvalent metal ions, for example to inhibit calcification of implanted substrates in contact with a patient's bodily fluids or tissues, and combinations thereof. Particularly advantageous materials are those well-suited, or specifically designed, for laser sintering or electron-beam melting manufacturing techniques, e.g., ASTM F-75 CoCr alloy, or Arcam Ti6Al4V ELI titanium alloy (available from Stratasys, Eden Prairie, Minn.). Ceramic materials, e.g., aluminum oxide or alumina, zirconium oxide or zirconia, compact of particulate diamond, and/or pyrolytic carbon maybe used with varying results.

Suitable synthetic polymers include, without limitation, polyamides (e.g., nylon), polyesters, polystyrenes, polyacrylates, vinyl polymers (e.g., polyethylene, polytetrafluoroethylene, polypropylene and polyvinyl chloride), polycarbonates, polyurethanes, polydimethyl siloxanes, cellulose acetates, polymethyl methacrylates, polyether ether ketones, ethylene vinyl acetates, polysulfones, nitrocelluloses, similar copolymers and mixtures thereof. Bioresorbable synthetic polymers can also be used such as dextran, hydroxyethyl starch, derivatives of gelatin, polyvinylpyrrolidone, polyvinyl alcohol, poly[N-(2-hydroxypropyl)methacrylamide], poly(hydroxy acids), poly(epsilon-caprolactone), polylactic acid, polyglycolic acid, poly(dimethyl glycolic acid), poly(hydroxy butyrate), and similar copolymers.

Other appropriate materials include, for example, the polyketone known as polyetheretherketone (PEEKT). This includes the material PEEK 450G, which is an unfilled PEEK approved for medical implantation available from Victrex of Lancashire, Great Britain. (Victrex is located at www.matweb.com or see Boedeker www.boedekencom). Other sources of this material include Gharda located in Panoli, India (www.ghardapolymers.com).

It should be noted that the material selected can also be filled. For example, other grades of PEEK are also available and contemplated, such as 30% glass-filled or 30% carbon filled, provided such materials are appropriate for use in implantable devices, typically those approved by the FDA or other regulatory body. Glass filled PEEK reduces the expansion rate and increases the flexural modulus of PEEK relative to that portion which is unfilled. The resulting product is known to be ideal for improved strength, stiffness, or stability. Carbon filled PEEK is known to enhance the compressive strength and stiffness of PEEK and lower its expansion rate. Carbon filled PEEK offers wear resistance and load carrying capability.

As will be appreciated, other suitable similar biocompatible thermoplastic or thermoplastic polycondensate materials that resist fatigue, have good memory, are flexible, are deflectable, have very low moisture absorption, and/or have good wear and/or abrasion resistance, can be used without departing from the scope of the disclosure. The implant can also be comprised of polyetherketoneketone (PEKK).

Other materials that can be used include polyetherketone (PEK), polyetherketoneetherketoneketone (PEKEKK), and polyetheretherketoneketone (PEEKK), and, generally, a polyaryletheretherketone. Further, other polyketones can be used as well as other thermoplastics.

Reference to appropriate polymers that can be used for the implant can be made to the following documents, all of which are incorporated herein by reference. These documents include: PCT Publication WO 02/02158 A1, dated Jan. 10, 2002 and entitled Bio-Compatible Polymeric Materials; PCT Publication WO 02/00275 A1, dated Jan. 3, 2002 and entitled Bio-Compatible Polymeric Materials; and PCT Publication WO 02/00270 A1, dated Jan. 3, 2002 and entitled Bio-Compatible Polymeric Materials.

The polymers used herein can be prepared by any of a variety of approaches including conventional polymer processing methods. Preferred approaches include, for example, injection molding, which is suitable for the production of polymer components with significant structural features, and rapid prototyping approaches, such as reaction injection molding and stereo-lithography. The substrate can be textured or made porous by either physical abrasion or chemical alteration to facilitate incorporation of the metal coating. Other processes are also appropriate, such as extrusion, injection, compression molding and/or machining techniques. Typically, the polymer is chosen for its physical and mechanical properties and is suitable for carrying and spreading the physical load between the joint surfaces.

More than one metal and/or polymer can be used in combination with each other. For example, one or more metal-containing substrates can be coated with polymers in one or more regions or, alternatively, one or more polymer-containing substrate can be coated in one or more regions with one or more metals.

The system or prosthesis can be porous or porous coated. The porous surface components can be made of various materials including metals, ceramics, and polymers. These surface components can, in turn, be secured by various means to a multitude of structural cores formed of various metals. Suitable porous coatings include, but are not limited to, metal, ceramic, polymeric (e.g., biologically neutral elastomers such as silicone rubber, polyethylene terephthalate and/or combinations thereof or combinations thereof. See, e.g., U.S. Pat. No. 3,605,123 to Hahn, issued Sep. 20, 1971; U.S. Pat. No. 3,808,606 to Tronzo issued May 7, 1974; U.S. Pat. No. 3,843,975 to Tronzo issued Oct. 29, 1974; U.S. Pat. No. 3,314,420 to Smith issued Apr. 18, 1967; U.S. Pat. No. 3,987,499 to Scharbach issued Oct. 26, 1976; and German Offenlegungsschrift 2,306,552, each of which is hereby incorporated by reference in its entirety. There can be more than one coating layer and the layers can have the same or different porosities. See, e.g., U.S. Pat. No. 3,938,198 to Kahn, et al., issued Feb. 17, 1976, which is hereby incorporated herein by reference in its entirety.

The coating can be applied by surrounding a core with powdered polymer and heating until cured to form a coating with an internal network of interconnected pores. The tortuosity of the pores (e.g., a measure of length to diameter of the paths through the pores) can be important in evaluating the probable success of such a coating in use on a prosthetic device. See, also, U.S. Pat. No. 4,213,816 to Morris issued Jul. 22, 1980, which is hereby incorporated herein by reference in its entirety. The porous coating can be applied in the form of a powder and the article as a whole subjected to an elevated temperature that bonds the powder to the substrate. Selection of suitable polymers and/or powder coatings can be determined in view of the teachings and references cited herein, for example based on the melt index of each.

An implant can include components and/or implant component parts produced via various methods. For example, in certain embodiments for a knee implant, the knee implant can include a metal femoral implant component produced by casting or by an additive manufacturing technique and having a patient-specific femoral intercondylar distance; a tibial component cut from a blank and machined to be patient-specific for the perimeter of the patient's cut tibia; and a tibial insert having a standard lock and a top surface that is patient-specific for at least the patient's intercondylar distance between the tibial insert dishes to accommodate the patient-specific femoral intercondylar distance of the femoral implant.

As another example, in certain embodiments a knee implant can include a metal femoral implant component produced by casting or by an additive manufacturing technique that is patient-specific with respect to a particular patient's M-L dimension and standard with respect to the patient's femoral intercondylar distance; a tibial component cut from a blank and machined to be patient-specific for the perimeter of the patient's cut tibia; and a tibial insert having a standard lock and a top surface that includes a standard intercondylar distance between the tibial insert dishes to accommodate the standard femoral intercondylar distance of the femoral implant.

Any of the materials listed above may be used with the associated manufacturing processes listed in Table 1 or Table 2 to manufacture a blank implant. In various embodiments, the blank is dimensioned to be, in one or more portions, only slightly larger than that of the implant. For example, the blank may be milled or cast such that all, or certain portions of the blank, are only slightly larger than the implant. Providing a blank from which material will be removed to arrive at the precise implant size, geometry and surface characteristics, can simplify the manufacturing processing and potentially ensure reproducibility.

The blank may be provided, e.g. by casting, milling, forging, compression molding, extruding or injection molding. A blank implant may be described as an implant that incorporates standard features of an "off-the shelf" implant, such as locking mechanisms, slots for coupling with bearing components, etc., but has at least one or more features that may be adapted in accordance with the image data of a patient's joint (e.g. perimeter size) in order to create an implant customized for that patient. For example, the outside geometry of the femoral component can be customized to be patient-specific or patient-matched. As an illustration, the width W and height H, and/or optionally the shape and dimensions of the entire articulating or outer surface, or portions thereof, can match/conform with that of the patient's corresponding joint surface.

Features of the implant that may be altered according to the patient's specific measurements of biological features can include any one or more of the illustrative measurements identified in Table 3.

TABLE 3

Exemplary patient-specific measurements of anatomical features
that can be used in the selection and/or design of an implant

| Anatomical feature | Exemplary measurement |
|---|---|
| Joint-line, joint gap | Location relative to proximal reference point |
| | Location relative to distal reference point |
| | Angle |
| | Gap distance between opposing surfaces in one or more locations |
| | Location, angle, and/or distance relative to contralateral joint |
| Soft tissue tension and/or balance | Joint gap distance |
| | Joint gap differential, e.g., medial to lateral |
| Medullary cavity | Shape in one or more dimensions |
| | Shape in one or more locations |
| | Diameter of cavity |
| | Volume of cavity |
| Subchondral bone | Shape in one or more dimensions |
| | Shape in one or more locations |
| | Thickness in one or more dimensions |
| | Thickness in one or more locations |
| | Angle, e.g., resection cut angle |
| Cortical bone | Shape in one or more dimensions |
| | Shape in one or more locations |
| | Thickness in one or more dimensions |
| | Thickness in one or more locations |
| | Angle, e.g., resection cut angle |
| Endosteal bone | Shape in one or more dimensions |
| | Shape in one or more locations |
| | Thickness in one or more dimensions |
| | Thickness in one or more locations |
| | Angle, e.g., resection cut angle |
| Cartilage | Shape in one or more dimensions |
| | Shape in one or more locations |
| | Thickness in one or more dimensions |
| | Thickness in one or more locations |
| | Angle, e.g., resection cut angle |
| Intercondylar notch | Shape in one or more dimensions |
| | Location |
| | Height in one or more locations |
| | Width in one or more locations |
| | Depth in one or more locations |
| | Angle, e.g., resection cut angle |
| Medial condyle | 2D and/or 3D shape of a portion or all |
| | Height in one or more locations |
| | Length in one or more locations |
| | Width in one or more locations |
| | Depth in one or more locations |
| | Thickness in one or more locations |
| | Curvature in one or more locations |
| | Slope in one or more locations and/or directions |
| | Angle, e.g., resection cut angle |
| Lateral condyle | 2D and/or 3D shape of a portion or all |
| | Height in one or more locations |
| | Length in one or more locations |
| | Width in one or more locations |
| | Depth in one or more locations |
| | Thickness in one or more locations |
| | Curvature in one or more locations |
| | Slope in one or more locations and/or directions |
| | Angle, e.g., resection cut angle |
| Trochlea | 2D and/or 3D shape of a portion or all |
| | Height in one or more locations |
| | Length in one or more locations |
| | Width in one or more locations |
| | Depth in one or more locations |
| | Thickness in one or more locations |
| | Curvature in one or more locations |
| | Slope in one or more locations and/or directions |
| | Angle, e.g., resection cut angle |
| Medial trochlea | 2D and/or 3D shape of a portion or all |
| | Height in one or more locations |
| | Length in one or more locations |
| | Width in one or more locations |
| | Depth in one or more locations |
| | Thickness in one or more locations |
| | Curvature in one or more locations |
| | Slope in one or more locations and/or directions |
| | Angle, e.g., resection cut angle |

TABLE 3-continued

Exemplary patient-specific measurements of anatomical features that can be used in the selection and/or design of an implant

| Anatomical feature | Exemplary measurement |
| --- | --- |
| Central trochlea | 2D and/or 3D shape of a portion or all<br>Height in one or more locations<br>Length in one or more locations<br>Width in one or more locations<br>Depth in one or more locations<br>Thickness in one or more locations<br>Curvature in one or more locations<br>Slope in one or more locations and/or directions<br>Angle, e.g., resection cut angle |
| Lateral trochlea | 2D and/or 3D shape of a portion or all<br>Height in one or more locations<br>Length in one or more locations<br>Width in one or more locations<br>Depth in one or more locations<br>Thickness in one or more locations<br>Curvature in one or more locations<br>Slope in one or more locations and/or directions<br>Angle, e.g., resection cut angle |
| Entire tibia | 2D and/or 3D shape of a portion or all<br>Height in one or more locations<br>Length in one or more locations<br>Width in one or more locations<br>Depth in one or more locations<br>Thickness in one or more locations<br>Curvature in one or more locations<br>Slope in one or more locations and/or directions<br>Angle, e.g., resection cut angle |
| Medial tibia | 2D and/or 3D shape of a portion or all<br>Height in one or more locations<br>Length in one or more locations<br>Width in one or more locations<br>Depth in one or more locations<br>Thickness in one or more locations<br>Curvature in one or more locations<br>Slope in one or more locations and/or directions<br>Angle, e.g., resection cut angle |
| Lateral tibia | 2D and/or 3D shape of a portion or all<br>Height in one or more locations<br>Length in one or more locations<br>Width in one or more locations<br>Depth in one or more locations<br>Thickness in one or more locations<br>Curvature in one or more locations<br>Slope in one or more locations and/or directions<br>Angle, e.g., resection cut angle |
| Entire patella | 2D and/or 3D shape of a portion or all<br>Height in one or more locations<br>Length in one or more locations<br>Width in one or more locations<br>Depth in one or more locations<br>Thickness in one or more locations<br>Curvature in one or more locations<br>Slope in one or more locations and/or directions<br>Angle, e.g., resection cut angle |
| Medial patella | 2D and/or 3D shape of a portion or all<br>Height in one or more locations<br>Length in one or more locations<br>Width in one or more locations<br>Depth in one or more locations<br>Thickness in one or more locations<br>Curvature in one or more locations<br>Slope in one or more locations and/or directions<br>Angle, e.g., resection cut angle |
| Central patella | 2D and/or 3D shape of a portion or all<br>Height in one or more locations<br>Length in one or more locations<br>Width in one or more locations<br>Depth in one or more locations<br>Thickness in one or more locations<br>Curvature in one or more locations<br>Slope in one or more locations and/or directions<br>Angle, e.g., resection cut angle |
| Lateral patella | 2D and/or 3D shape of a portion or all<br>Height in one or more locations<br>Length in one or more locations |

TABLE 3-continued

Exemplary patient-specific measurements of anatomical features that can be used in the selection and/or design of an implant

| Anatomical feature | Exemplary measurement |
|---|---|
| Femoral head | Width in one or more locations<br>Depth in one or more locations<br>Thickness in one or more locations<br>Curvature in one or more locations<br>Slope in one or more locations and/or directions<br>Angle, e.g., resection cut angle<br>2D and/or 3D shape of a portion or all<br>Height in one or more locations<br>Length in one or more locations<br>Width in one or more locations<br>Depth in one or more locations<br>Thickness in one or more locations<br>Curvature in one or more locations<br>Slope in one or more locations and/or directions<br>Angle, e.g., resection cut angle |
| Acetabulum | 2D and/or 3D shape of a portion or all<br>Height in one or more locations<br>Length in one or more locations<br>Width in one or more locations<br>Depth in one or more locations<br>Thickness in one or more locations<br>Curvature in one or more locations<br>Slope in one or more locations and/or directions<br>Angle, e.g., resection cut angle |
| Glenoid | 2D and/or 3D shape of a portion or all<br>Height in one or more locations<br>Length in one or more locations<br>Width in one or more locations<br>Depth in one or more locations<br>Thickness in one or more locations<br>Curvature in one or more locations<br>Slope in one or more locations and/or directions<br>Angle, e.g., resection cut angle |
| Humeral head | 2D and/or 3D shape of a portion or all<br>Height in one or more locations<br>Length in one or more locations<br>Width in one or more locations<br>Depth in one or more locations<br>Thickness in one or more locations<br>Curvature in one or more locations<br>Slope in one or more locations and/or directions<br>Angle, e.g., resection cut angle |
| Ankle joint | 2D and/or 3D shape of a portion or all<br>Height in one or more locations<br>Length in one or more locations<br>Width in one or more locations<br>Depth in one or more locations<br>Thickness in one or more locations<br>Curvature in one or more locations<br>Slope in one or more locations and/or directions<br>Angle, e.g., resection cut angle |
| Elbow | 2D and/or 3D shape of a portion or all<br>Height in one or more locations<br>Length in one or more locations<br>Width in one or more locations<br>Depth in one or more locations<br>Thickness in one or more locations<br>Curvature in one or more locations<br>Slope in one or more locations and/or directions<br>Angle, e.g., resection cut angle |
| Wrist | 2D and/or 3D shape of a portion or all<br>Height in one or more locations<br>Length in one or more locations<br>Width in one or more locations<br>Depth in one or more locations<br>Thickness in one or more locations<br>Curvature in one or more locations<br>Slope in one or more locations and/or directions<br>Angle, e.g., resection cut angle |
| Hand | 2D and/or 3D shape of a portion or all<br>Height in one or more locations<br>Length in one or more locations<br>Width in one or more locations<br>Depth in one or more locations<br>Thickness in one or more locations |

TABLE 3-continued

Exemplary patient-specific measurements of anatomical features that can be used in the selection and/or design of an implant

| Anatomical feature | Exemplary measurement |
|---|---|
| | Curvature in one or more locations |
| | Slope in one or more locations and/or directions |
| | Angle, e.g., resection cut angle |
| Finger | 2D and/or 3D shape of a portion or all |
| | Height in one or more locations |
| | Length in one or more locations |
| | Width in one or more locations |
| | Depth in one or more locations |
| | Thickness in one or more locations |
| | Curvature in one or more locations |
| | Slope in one or more locations and/or directions |
| | Angle |
| Spine | 2D and/or 3D shape of a portion or all |
| | Height in one or more locations |
| | Length in one or more locations |
| | Width in one or more locations |
| | Depth in one or more locations |
| | Thickness in one or more locations |
| | Curvature in one or more locations |
| | Slope in one or more locations and/or directions |
| | Angle, e.g., resection cut angle |
| Spinal facet joint | 2D and/or 3D shape of a portion or all |
| | Height in one or more locations |
| | Length in one or more locations |
| | Width in one or more locations |
| | Depth in one or more locations |
| | Thickness in one or more locations |
| | Curvature in one or more locations |
| | Slope in one or more locations and/or directions |
| | Angle, e.g., resection cut angle |

In accordance with other embodiments, a joint implant is presented wherein at least one surface of the implant rests on subchondral bone, and advantageously does not require invasive cutting of bone. These implants may be made by the methods described hereinabove. While an exemplary knee implant is described, it is to be understood that the joint implant may be associated with, for example, a shoulder, a hip, a vertebrae, an elbow, an ankle, a hand, a foot or a wrist.

Figure 3:
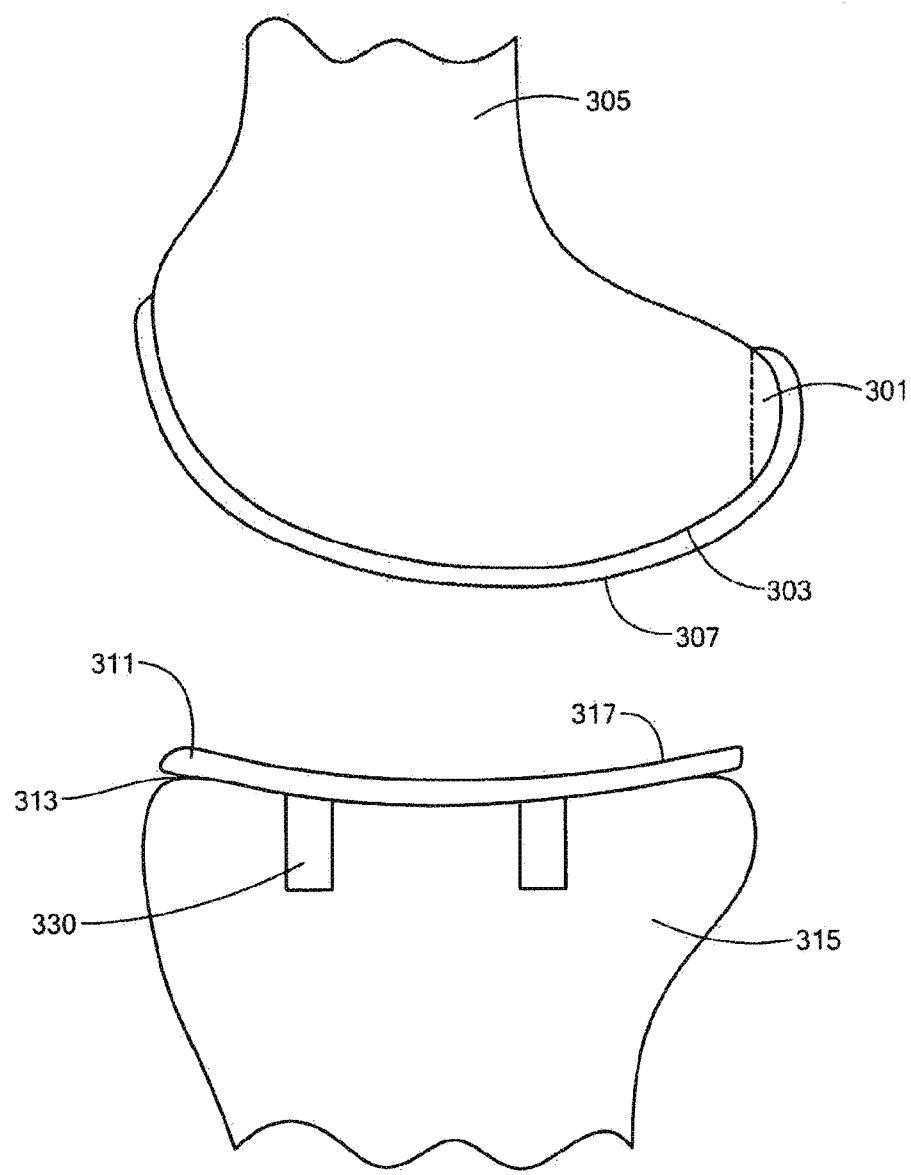
FIG. 3 shows an embodiment of a total knee implant, in cross-sectional view.

FIG. 3 shows in cross-section a total knee implant, in accordance with one embodiment. A femoral component 301 includes a first femoral component surface 303 for securing to a surgically prepared compartment of a distal end of a femur 305. A second femoral component surface 307 desirably replicates the shape of the femoral condyle(s).

A tibial component 311 includes a first tibial component surface 313 for resting on and contacting a proximal surface of the tibia. The proximal surface of the tibia may advantageously include substantially uncut subchondral bone. In illustrative embodiments, at least a portion of the first tibial component surface 313 is substantially a negative of or conforms to the proximal surface. For example, a three-dimensional image of the proximal surface may be obtained as described above, with the first tibial component surface 313 manufactured based on the three-dimensional image. A second tibial component surface 317 articulates with the second femoral component surface 307. It is to be understood that in a total knee joint implant, the tibial component(s) can cover both the medial and lateral plateau. In various embodiments, the tibial component may be a single component that covers both the medial and lateral plateau (and may or may not leave the tibial spines intact), or may include two components (i.e., a tibial component for the medial side and a tibial component for the lateral side). In other embodiments, for example, a unicondylar knee implant, the tibial component may cover either only the medial or lateral plateau.

In an exemplary embodiment, the femoral component 301 and the tibial component 311 may each be approximately 2-3 mm thick. The thickness may be, for example, similar to the thickness of cartilage removed in preparing the joint for implantation. Thus, overstuffing of the joint is desirably minimized while providing a non-invasive or less-invasive alternative to traditional invasive knee surgery. By following the teaching of the present disclosure, the manufacture of such implants having the requisite dimensions and strength can be easily achievable. Some or all of the cartilage on the femoral and/or tibial articular surfaces may be removed to prepare the joint for receiving an implant (i.e., to expose some or all of the subchondral bone) as necessary, depending on the progression of cartilage wear, disease, etc. The interior surfaces of the femoral and/or tibial component may be accordingly designed so that the implant may be affixed directly to the desired exposed area(s) of subchondral bone. The thickness and/or shape of the femoral and/or tibial components may be determined (e.g., so as to reconstruct the thickness of the originally present articular cartilage) from an image-derived subchondral bone shape of the joint surfaces, as described in U.S. application Ser. No. 10/305,652.

To provide a desired implant strength (e.g., for biomechanical loading) and reliability, and still be thin enough (or of a desired size or shape) to avoid overstuffing the joint, the first tibial surface 313 and/or the second tibial surface 317 may include, without limitation, a metal and/or a ceramic. For example, the second femoral component surface 307 may include at least one of a ceramic and a metal, and the second tibial component surface 317 includes at least one of a ceramic and a metal. In another example, both the second femoral component surface 307 and the second tibial surface 317 include a metal. In still another example, both the second femoral component surface 307 and the second tibial surface 317 include a ceramic. In yet another example, the second femoral component surface 307 includes one of a ceramic and a metal, and the second tibial surface 317 includes the other of the one of a ceramic and a metal.

In various embodiments, the knee implant includes an anchoring mechanism 330. The anchoring mechanism 330 may be, without limitation, a peg and/or a keel protruding from the first tibial surface 313.

Implant components generated by different techniques can be assessed and compared for their accuracy of shape relative to the intended shape design, for their mechanical strength, and for other factors. In this way, different manufacturing techniques can supply other considerations for achieving an implant component design with one or more target features.

The disclosed methods may use a wide variety of materials, including, but not limited to, plastics, metals, crystal free metals, ceramics, biological materials (e.g., collagen or other extracellular matrix materials), hydroxyapatite, cells (e.g., stem cells, chondrocyte cells or the like), or combinations thereof. Based on the information (e.g., measurements and/or calculations) obtained regarding the defect and the articular surface and/or the subchondral bone, a repair material can be formed or selected. Further, using one or more of these techniques described herein, a cartilage replacement or regenerating material having a curvature that will fit into a particular cartilage defect, desirably following the contour and shape of the articular surface, and further desirably matching the thickness of the surrounding cartilage. The repair material can include any combination of materials, and typically includes at least one non-pliable material, for example materials that are not easily bent or changed.

Assessment/Evaluation Systems

Applicant's disclosure also includes the realization that there are numerous factors that may be relevant to the optimal creation of a joint implant, which may skew or otherwise alter a desired blank choice and/or chosen manufacturing method(s) for various reasons. As previously noted, these factors should desirably be taken into consideration during the implant planning process. In addition, the importance and/or criticality of one or more of these factors may be reduced, or may rise to a level of "absolutely necessary" during certain situations, and it is highly desirably that any assessment system consider many if not all of these factors when planning the manufacturing and/or modification process in the creation of a patient-specific implant. Desirably, the proper consideration of such factors will result in choice and creation of an optimal implant that satisfies other user requirements/desires, such as price, time or implant availability, design strength or durability, or other user or system defined requirements.

As previously noted, one or more factors may include assessing the available methods for altering the implant shape and/or size from the blank to the final implant. Additive and subtractive processing techniques may be limited in their applicability, and the assessment system should be capable of evaluating multiple processing types and approaches to obtain a desired implant from one or more blanks. For example, a potential assessment system may determine a first set of manufacturing steps required to increase various dimensions (using additive manufacturing steps) on a first blank to obtain a desired implant size. The same assessment system may determine a second set of manufacturing steps required to decrease various dimensions (using subtractive manufacturing steps) on a second blank to obtain the same desired implant size. The system may then evaluate the two sets of manufacturing steps to determine which set may be more desirable according to pre-determined criteria or, alternatively, to implant-specific criteria entered by a user during the specific implant creation process (i.e., the user determines that cost for an implant is more critical than manufacturing time, so the assessment system may choose or weigh more heavily a more cost-effective manufacturing method). As previously noted, a wide variety of potential factors may be evaluated to determine an optimal method of manufacturing the implant, and the assessment system could optionally combine various manufacturing methods in its assessment of the manufacturing steps contributing to a single implant (i.e., using both additive and subtractive manufacturing on a single blank to create a desired implant thickness and/or shape).

In a similar manner, the costs of manufacturing an implant for patient-specific use may be a factor utilized in determining the type of implant used, in a similar manner to methods of manufacture. Such costs can include raw material costs for the implant blank, as well as manufacturing costs to reach the blank stage. Further costs can include costs relating to differing types and degrees of manufacturing (i.e., costs for various depths of additive or subtractive manufacturing, as well as operating costs for equipment, personnel, consumables, etc.). Additional cost factors could include shipping and material treatment costs (i.e., differing coating, surface treatments, polishing, passivation and/or sterilization requirements relating to different manufacturing methods) as well as others.

An additional factor could include the availability of materials and equipment for manufacturing the desired implant. The availability and location of various sized blanks may be limited, and it may be desirable to assess different blanks (as well as blanks that may be manufactured "on demand" or "just in time") to determine the most suitable relating to the various weighted factors. In a similar manner, the presence and availability of required process and manufacturing equipment should be assessed, as equipment for one manufacturing method, currently sitting idle and/or underutilized, may be more desirable than other equipment (for other manufacturing methods) being currently used at or near full capacity. Similarly, a blank located near the manufacturing facility may be deemed more desirable than one located a continent away.

Another additional factor could include the time required for manufacturing the desired implant from the various available blanks Differing manufacturing methods will likely require differing amounts of processing time, as well as any additional post-processing (i.e., cleaning, passivating, coating, surface treatment, sterilization, etc.), and time may be a critical commodity (i.e., surgery is scheduled in 48 hours), or may not be a significant factor (i.e., surgery will be scheduled when the implant is available).

Another potential factor could include the accuracies and/or shapes/tolerances obtainable by each manufacturing method. For example, if accuracy of shape relative to the intended shape design is deemed critical to a particular patient's implant component design, then the manufacturing technique supplying the most accurate shape can be selected. If a minimum implant thickness is critical to a particular patient's implant component design, then the manufacturing technique supplying the highest mechanical strength and therefore allowing the most minimal implant component thickness, can be selected. Branner et al. describe a method a method for the design and optimization of additive layer manufacturing through a numerical coupled-field simulation, based on the finite element analysis (FEA). Branner's method can be used for assessing and comparing product mechanical strength generated by different additive layer manufacturing techniques, for example, SLM, DMLS, and LC.

It may also be desirous to account for differing material types, strengths and/or durability when designing and/or manufacturing an implant. For example, material additive processes are often limited to certain types of materials (i.e., powders and/or fluids) that may have various structural limitations—various manufacturing methods may create an implant highly resistant to compressive loading, but possibly less resistant to torsional and/or tensive loading as compared to a cast or wrought implant created using machining methods. Similarly, various material removal methods may alter the strength of materials in undesirable or unaccounted for ways, such as heat generation and/or micro-fracture due to interaction with a cutting head, or various manufacturing methods may harden or strengthen materials in other ways. In concert, the different types of materials and manufacturing methods utilized may necessitate different minimal or maximal implant thicknesses to achieve the desire implant strength or durability, which may impact the final implant design in ways that affect the suitability of different size blanks as related to the final implant. In addition, different manufacturing methods may also create different types of surfaces best suited to different purposes, such as, for example, a material additive process which can (if desired) create a relatively porous structure (possibly suited for bone in-growth and/or cement interdigitation, and thus better suited for a bone-facing surface of the implant), while a material subtractive process may create a relatively smooth, hard surface (possibly suited for an articulating surface of the implant, and thus better suited for a joint-facing surface of the implant).

In a similar manner, numerous other relevant factors can utilized to determine a desired and/or appropriate construction of a desired implant. Aside from strength and design factors, other factors such as cost, manufacturing time, available manufacturing and machining equipment and trained personnel, competing priorities, geographic location of equipment and supplies, current blank inventory, implant features, materials, implant durability requirements, transportation costs and availability, etc., may contribute to the final choice of blank and manufacturing method (or combination of methods) to create a designed implant.

An additional exemplary listing of features that may be altered to create a patient specific implant from a blank implant is included in Table 4.

TABLE 4

Exemplary implant features that can be selected and/or designed based on patient-specific measurements

| | |
|---|---|
| Implant or implant or component (applies to most implants and implant components) | One or more portions of, or all of, an external implant component curvature |
| | One or more portions of, or all of, an internal implant dimension |
| | One or more portions of, or all of, an internal or external implant angle |
| | Portions or all of one or more of the ML, AP, SI dimension of the internal and external component and component features |
| | An outer locking mechanism dimension between a plastic or non-metallic insert and a metal backing component in one or more dimensions |
| | Component height |
| | Component profile |
| | Component 2D or 3D shape |
| | Component volume |
| | Composite implant height |
| | Insert width |
| | Insert shape |
| | Insert length |
| | Insert height |
| | Insert profile |
| | Insert curvature |
| | Insert angle |
| | Distance between two curvatures or concavities |
| | Polyethylene or plastic width |
| | Polyethylene or plastic shape |
| | Polyethylene or plastic length |
| | Polyethylene or plastic height |
| | Polyethylene or plastic profile |
| | Polyethylene or plastic curvature |
| | Polyethylene or plastic angle |
| | Component stem width |
| | Component stem shape |
| | Component stem length |
| | Component stem height |
| | Component stem profile |
| | Component stem curvature |
| | Component stem position |
| | Component stem thickness |
| | Component stem angle |
| | Component peg width |
| | Component peg shape |
| | Component peg length |
| | Component peg height |
| | Component peg profile |
| | Component peg curvature |
| | Component peg position |
| | Component peg thickness |

TABLE 4-continued

Exemplary implant features that can be selected and/or designed based on patient-specific measurements

| | |
|---|---|
| | Component peg angle |
| | Slope of an implant surface |
| | Number of sections, facets, or cuts on an implant surface |
| Femoral implant or implant component | Condylar distance of a femoral component, e.g., between femoral condyles |
| | A condylar coronal radius of a femoral component |
| | A condylar sagittal radius of a femoral component |
| Tibial implant or implant component | Slope of an implant surface |
| | Condylar distance, e.g., between tibial joint-facing surface concavities that engage femoral condyles |
| | Coronal curvature (e.g., one or more radii of curvature in the coronal plane) of one or both joint-facing surface concavities that engage each femoral condyle |
| | Sagittal curvature (e.g., one or more radii of curvature in the sagittal plane) of one or both joint-facing surface concavities that engage each femoral condyle |

Figure 4:
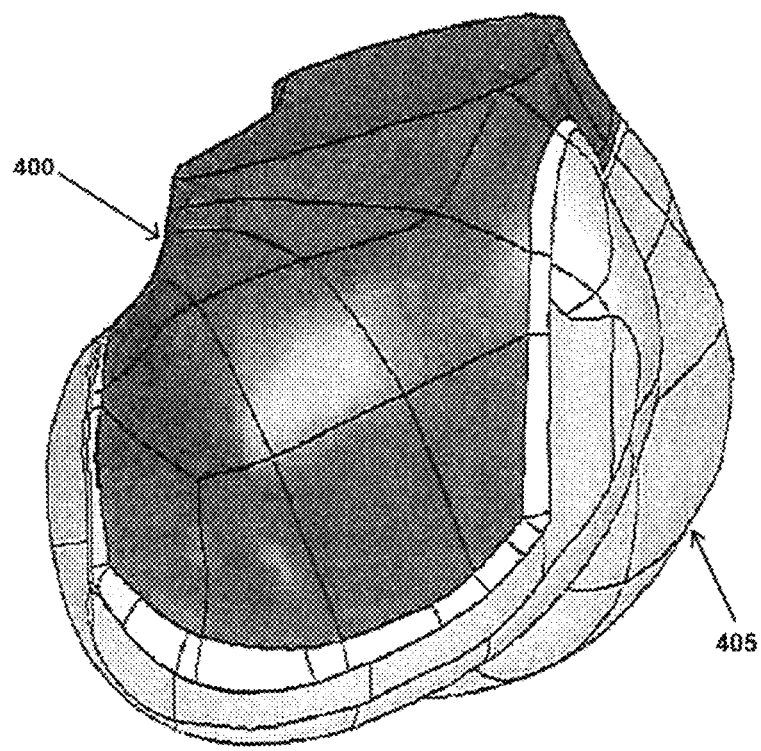
FIG. 4 is a side perspective view of a femoral implant implanted on a femur.
Figure 5:
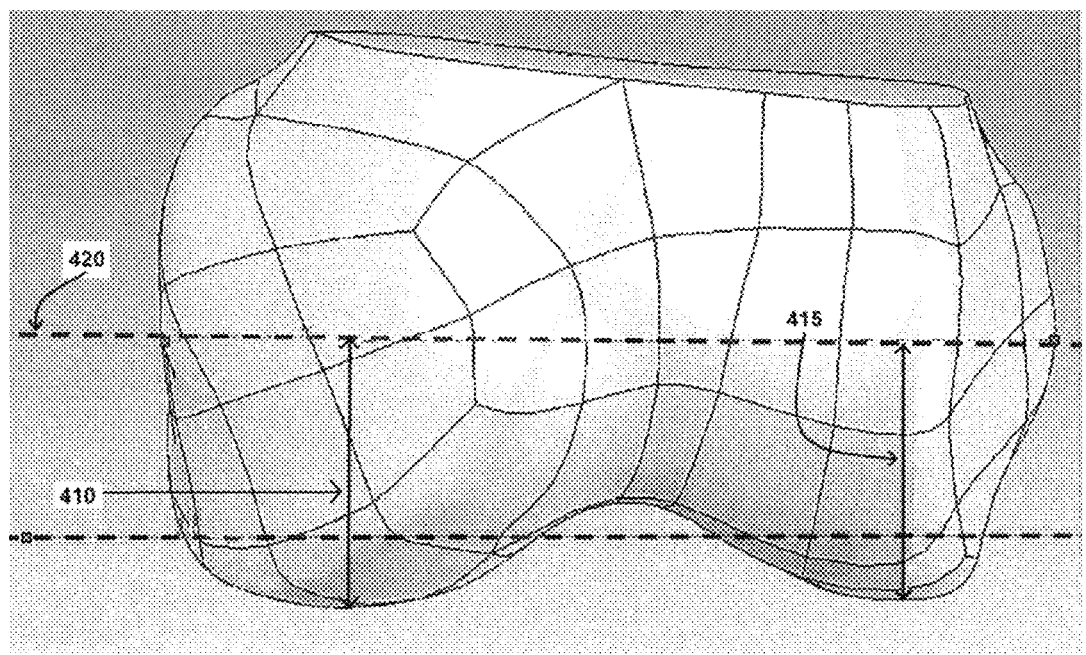
FIG. 5 is a 3-dimensional view of the end of a femur.

FIG. 4 shows a standard femoral implant 405 correctly fitted and seated on a femur 400. In order to obtain a correct fit, in accordance with one embodiment, a three-dimensional model may be used to measure dimensions of the patient's joint. FIG. 5 depicts measurements of medial condyle height 410 and lateral condyle heights 415 (relative to an epicondylar axis 420) on a femur. Based on these measurements, a blank implant could be tailored to the exact dimensions of the patient's joint using the described methods. Any of the patient measurements listed in Table 3 may dictate what modifications may be needed to alter the blank implant using any of the manufacturing process listed in Table 2 in order to customize the blank implant. For example, once a patient's image data is analyzed, a blank implant is selected and then may be machined to carve out or increase the patella track, if necessary, of the implant based on the configuration of the patient's joint. The size of the perimeter of the implant, the shape of the perimeter of the implant, the width of the implant, the height of the implant, are but a few of the geometrical adjustments that may be made to the blank in order to render an implant that conforms to the patient's joint. Additional features may be adjusted as well, such as, the intercondylar notch area may be machined for line or area contact with the articular surfaces of a tibial component of various degrees of flexion.

In addition to the above discussion of altering a blank by removing material, adding material to a blank using any of the process listed in Table 2 may also be considered. Again, any of the geometrical measurements may be altered using an additive manufacturing process in order to incorporate additional material onto the blank implant. Additional features may also be incorporated using an additive process, such as adding material to one condyle of a femoral component in order to compensate for a varus or valgus deformity.

The foregoing description of embodiments has been provided for the purposes of illustration and description. It is not intended to be exhaustive or to limit the disclosure to the precise forms disclosed. Many modifications and variations will be apparent to the practitioner skilled in the art. The embodiments were chosen and described in order to best explain the principles and practical applications, thereby enabling others skilled in the art to understand the inventions and the various embodiments and with various modifications that are suited to the particular uses contemplated.

What is claimed is:

1. A method of making a knee implant system for repairing a knee joint of a patient, comprising:
 a. determining a three-dimensional shape of at least a portion of an articular surface of the knee joint of the patient from electronic image data of the knee joint of the patient;
 b. altering a first blank implant to form a femoral implant, wherein at least a portion of an articulating surface of the femoral implant conforms to the three-dimensional shape, wherein the femoral implant further includes one or more femoral standard features;
 c. altering a second blank implant to form a tibial implant, wherein at least a portion of an articulating surface of the tibial implant complements a corresponding portion of the articulating surface of the femoral implant, wherein the tibial implant includes one or more tibial standard features.

2. The method of claim 1, wherein the corresponding portion of the articulating surface of the femoral implant conforms to the three-dimensional shape.

3. The method of claim 1, wherein the corresponding portion of the articulating surface of the femoral implant includes the one or more femoral standard features.

4. The method of claim 1, wherein the one or more femoral standard features includes a standard intercondylar distance.

5. The method of claim 4, wherein the one or more tibial standard features includes a feature configured based on the standard intercondylar distance.

6. The method of claim 1, wherein the one or more femoral standard features includes a standard anchoring mechanism for the femoral implant.

7. The method of claim 1, wherein altering a first or second blank implant includes subtracting and/or adding material to one or more portions of the first or second blank implant.

* * * * *